(12) United States Patent
Merz

(10) Patent No.: US 9,457,414 B2
(45) Date of Patent: Oct. 4, 2016

(54) PLIERS FOR CUTTING WORKPIECES

(76) Inventor: Alexander Merz, Seitingen (DE)

( * ) Notice: Subject to any disclaimer, the term of this patent is extended or adjusted under 35 U.S.C. 154(b) by 299 days.

(21) Appl. No.: 14/002,214

(22) PCT Filed: Mar. 2, 2012

(86) PCT No.: PCT/EP2012/053647
§ 371 (c)(1),
(2), (4) Date: Nov. 4, 2013

(87) PCT Pub. No.: WO2012/117096
PCT Pub. Date: Sep. 7, 2012

(65) Prior Publication Data
US 2014/0053411 A1   Feb. 27, 2014

(30) Foreign Application Priority Data

Mar. 2, 2011  (DE) .................. 10 2011 001 013

(51) Int. Cl.
| B23D 29/02 | (2006.01) |
|---|---|
| A61B 17/88 | (2006.01) |
| B25B 7/12 | (2006.01) |
| B26B 17/02 | (2006.01) |

(52) U.S. Cl.
CPC ......... B23D 29/023 (2013.01); A61B 17/8863 (2013.01); B25B 7/12 (2013.01); B26B 17/02 (2013.01)

(58) Field of Classification Search
CPC ..... A61B 17/8863; B25B 7/12; B26B 17/02; B23D 29/023
See application file for complete search history.

(56) References Cited

U.S. PATENT DOCUMENTS

| 401,308 | A |  | 4/1889 | Selleck |  |
|---|---|---|---|---|---|
| 1,820,169 | A | * | 8/1931 | Wigand | B25B 7/04 30/190 |
| 2,385,835 | A | * | 10/1945 | Neal | B23D 29/023 30/250 |
| 3,210,844 | A | * | 10/1965 | Tontscheff | B23D 29/023 30/192 |
| 3,716,879 | A |  | 2/1973 | Boyajian |  |
| 4,058,893 | A | * | 11/1977 | Boyajian | B23D 29/023 30/189 |
| 4,176,450 | A | * | 12/1979 | Muromoto | B26D 3/169 30/251 |
| 4,312,127 | A | * | 1/1982 | Tanaka | B23D 21/10 30/250 |
| 4,891,883 | A |  | 1/1990 | Mantele |  |
| 5,187,869 | A |  | 2/1993 | Heiss |  |
| 7,886,446 | B2 | * | 2/2011 | Yu Chen | B26B 13/26 30/175 |
| 9,066,473 | B2 | * | 6/2015 | Podlesny | A01G 3/021 |
| 2008/0000091 | A1 |  | 1/2008 | Eriguchi |  |
| 2014/0053411 | A1 | * | 2/2014 | Merz | A61B 17/8863 30/240 |

FOREIGN PATENT DOCUMENTS

| AT |  | 17406 B |  | 8/1904 |
|---|---|---|---|---|
| DE |  | 3302875 A1 |  | 8/1984 |
| DE |  | 4329220 A1 |  | 3/1995 |
| EP |  | 0321884 A2 |  | 6/1989 |
| EP |  | 0454615 A1 |  | 10/1991 |
| WO | WO 2012/117096 A1 | * | 9/2012 |

* cited by examiner

*Primary Examiner* — Hwei C Payer
(74) *Attorney, Agent, or Firm* — Bachman & LaPointe, P.C.

(57) ABSTRACT

A pliers for cutting workpieces, in particular workpieces made of metal, comprising at least one plier leg (1) and a pressure element (2), which are connected to each other by a rotation point (13), wherein the plier leg (1) forms a jaw (8) for receiving the workpiece. A cutting element (18) with a cutting mouth (19) is associated with the plier leg (1), wherein a bottom of the jaw (8) and a bottom of the cutting mouth (19) are arranged in the vicinity of a rotation point (29) about which the cutting element (18) is rotating in the plier leg (1).

8 Claims, 3 Drawing Sheets

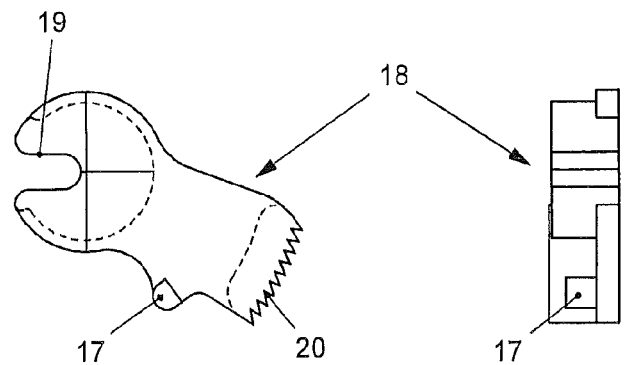
Fig. 5  Fig. 6
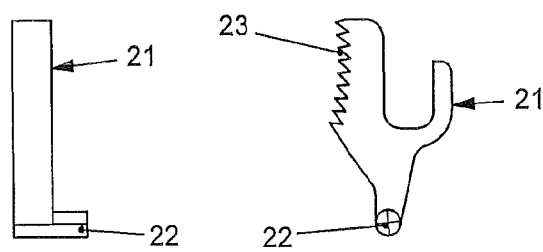
Fig. 7  Fig. 8
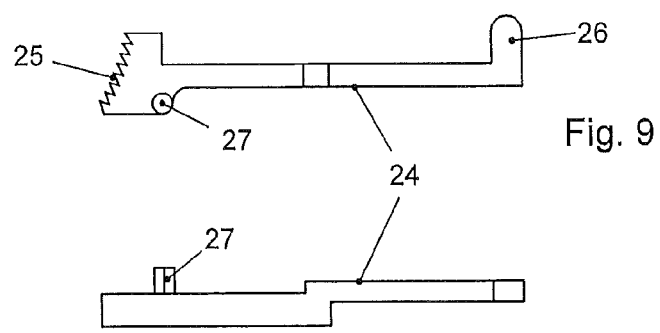
Fig. 9
Fig. 10

PLIERS FOR CUTTING WORKPIECES

BACKGROUND OF THE INVENTION

The invention relates to a pair of pliers for cutting workpieces, in particular workpieces of metal, said pliers having at least one leg and one pressure element which are connected together by means of a pivot point, wherein the leg of the pliers realizes a jaw of the pliers for receiving the workpiece.

Varied designs of pliers are known and are on the market. The present case is concerned above all with special pliers for cutting workpieces in accident surgery. They are required, for example in orthopedics to nip off wires, nails or screw-type elements. In this case, the prevention of splinters or similar particles of the workpiece during the separating operation is a hygienic necessity to avoid infections. In the case of intraosseous wires in the operative handling of fractures, bone fragments with wires, in the majority of cases with so-called "Kirschner" wires are connected together. Side cutters or similar tools are used to cut off said wires, which, however, also involves the risk of workpiece residues. In addition, considerable forces have to be applied to the pliers in order to cut the corresponding wire.

Such medical or surgical pliers are known, for example, from EP 0 321 884. Using said wire pliers, a wire is pinched-off, which requires considerable force. The same also applies to the pliers as claimed in EP 0 454 615 or DE 43 29 220 A1.

The object of the present invention is, on the one hand, to develop a pair of pliers of the above-mentioned type which is able to be operated with one hand and which does not require a very high level of force to be expended, additionally, however, does not result in any workpiece waste which can remain behind.

SUMMARY OF THE INVENTION

To achieve the object, on the one hand, the leg of the pliers has associated therewith a cutting element with a cutting jaw, wherein a bottom of the jaw of the pliers and a bottom of the cutting jaw are arranged in the vicinity of a pivot point about which the cutting element rotates in the leg of the pliers.

As a result, the wire is not pinched-off, but is actually cut. The cutting element is rotated about the pivot point and at the same time cuts into the workpiece by way of a cutting edge such that said workpiece is actually cut off once the rotation has been completed. This avoids, on the one hand, splinters or the like being created and, on the other hand, reduces the force expended.

Independent protection is additionally sought for the leg of the pliers having associated therewith a cutting element with a cutting jaw, wherein the contours of the jaw of the pliers and of the cutting jaw are matched to one another and the cutting element rotates in a roller cage in the leg of the pliers.

The advantage of this is that there is controlled interaction between the jaw of the pliers and the cutting jaw. The cutting element is held over a large part of its periphery by the roller cage and is guided in a secured manner about a pivot point during the rotation.

In addition, protection is sought independently for the leg of the pliers to have associated therewith a cutting element with a cutting jaw and the cutting element to be arranged by means of a latching device so as to be rotatable about a pivot point in relation to the leg of the pliers.

Said latching device is particularly important. The necessary force expended is reduced considerably by its actuation. The actuation of the latching device is also not effected in a continuous manner, but in a preferred manner by means of quasi pumping the leg of the pliers or the pressure element in relation to the leg of the pliers.

In a preferred exemplary embodiment, the cutting element is to have a latching toothing located opposite the cutting jaw. Said latching toothing interacts with a toothed strip of a pressure piece, said pressure piece being actuated by the pressure element. To this end, the pressure piece is supported by way of a round piece in a depression in the pressure element. If the pressure element is actuated, the pressure piece with the toothed strip, which engages in the latching toothing of the cutting element, entrains said cutting element and rotates it about the pivot point. As a result, a necessary expending of force is minimized.

So that the pressure piece or the toothed strip remain engaged with the latching toothing, the pressure piece is to have associated therewith another corresponding force storing means which presses onto the pressure piece in such a manner that the toothed strip engages with the latching toothing.

In order to make possible an above-mentioned pumping, that is to say resetting the pressure piece on the latching toothing, another fixing means is to be provided which holds the cutting element in the position of rotation already achieved when the pressure piece is reset. To this end, the fixing means also has a latching strip which engages in the latching toothing of the cutting element. In a simple exemplary embodiment, the fixing means is arranged so as to be displaceable in the toothed leg.

In a preferred manner, the pressure element is realized in the manner of a leg and has a pivot-joint-like connection to the leg of the pliers. To this end, a pivot pin which sits in a pivot depression in the leg of the pliers is provided on the pressure element.

So that a forcing apart of the leg of the pliers and the pressure element is improved, a corresponding force storing means is to be provided between said leg of the pliers and said pressure element. In this case, this can be a spring-mounted bolt.

BRIEF DESCRIPTION OF THE DRAWINGS

Further advantages, features and details of the invention are produced from the following description of preferred exemplary embodiments as well as by way of the drawing, in which:

FIG. 5 shows a scaled down top view of a cutting element for the pliers according to FIG. 1;

FIG. 6 shows a top view of the cutting element according to FIG. 5 rotated by 90°;

FIG. 7 shows a side view of a pressure piece from the pliers according to FIG. 1;

FIG. 8 shows a top view of the pressure piece according to FIG. 7;

FIG. 9 shows a top view of a fixing means for the pliers as claimed in the invention according to FIG. 1;

FIG. 10 shows a side view of the fixing means according to FIG. 9;

DETAILED DESCRIPTION

Figure 1:
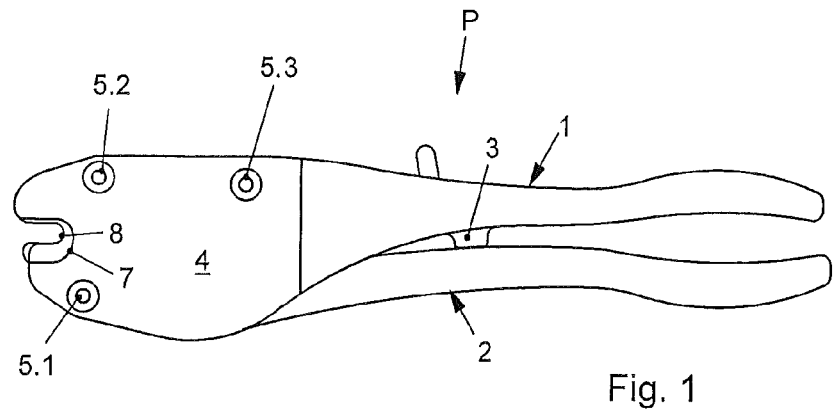
FIG. 1 shows a top view of a pair of pliers as claimed in the invention for cutting workpieces (not shown in any detail)

A pair of pliers P as claimed in the invention for cutting workpieces (not shown in any detail) has a leg 1 of the pliers and a leg-like pressure element 2 which is associated with the leg 1 of the pliers. The leg 1 of the pliers is supported in the closed position against the pressure element 2 by means of a stop 3. It is possible for the stop 3 to be realized in an elastic manner in this case.

A cover 4, which conceals the essential functional elements of the pliers P, can be seen in the front region of the leg 1 of the pliers. The cover 4, in this case, is connected to the leg 1 of the pliers by means of three screw bolts 5.1 to 5.3. The screw bolts 5.1 to 5.3 engage in the threaded bores 6.1 to 6.3 of the leg 1 of the pliers, as is shown in FIG. 2.

In addition, the cover 4 frames a jaw of the pliers 8, which is realized by the leg 1 of the pliers, by means of a recess 7.

Figure 2:
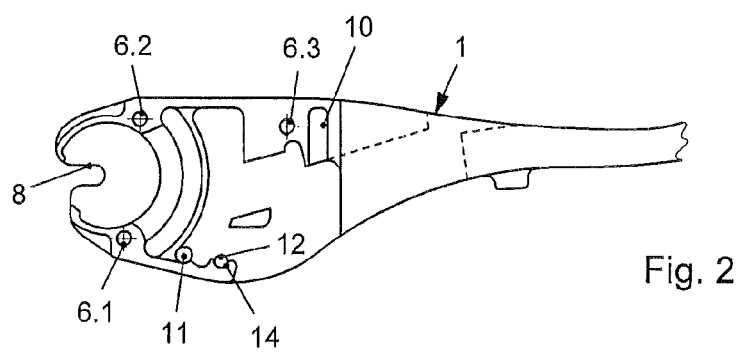
FIG. 2 shows a partial top view of a leg of the pliers of the pliers according to FIG. 1.
Figure 3:
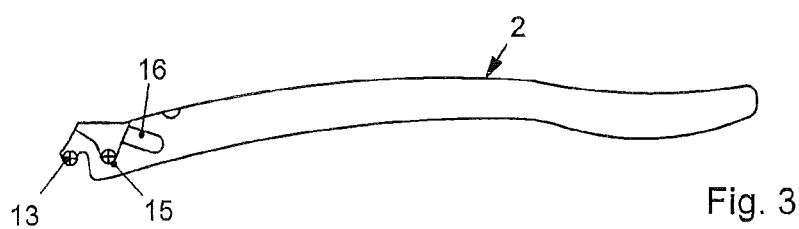
FIG. 3 shows a scaled down top view of a pressure element of the pliers according to FIG. 1.
Figure 4:
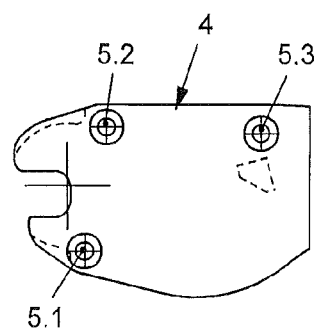
FIG. 4 shows a top view of a cover for the pliers according to FIG. 1.

It can also be seen in FIG. 2 that a guide channel 9 and a blind hole 10 are provided in the leg 1 of the pliers. In addition, receiving means 11 and 12 are realized. The receiving means 11 serves for the bearing arrangement of a stop (to be described later), the receiving means 12 serves for the bearing arrangement of a pivot pin 13 (see FIG. 3), by way of which the pressure element 2 sits in a pivot depression 14 in the leg 1 of the pliers. Along with said pivot pin 13, a depression 15 for receiving a round piece of a pressure piece (to be described later) is realized in the pressure element 2, according to FIG. 3. A further blind hole 16 is open toward said depression 15.

A guide pin 17, which projects from a cutting element 18 according to FIGS. 5 and 6, engages in the above-mentioned guide channel 9. Said cutting element 18 has a cutting jaw 19 the contours of which imitate the jaw 8 of the pliers. A latching toothing 20 is provided on the cutting element 18 opposite the cutting jaw 19.

The above-mentioned pressure piece 21, which is supported in the depression 15 of the pressure element 2 by means of a round piece 22, is shown in FIGS. 7 and 8. Said pressure piece 21 has a toothed strip 23. A fixing means 24 is shown in FIGS. 9 and 10. Said fixing means 24 has a latching strip 25 and a draw hook 26 which is located opposite said latching strip. A stop cam 27 is also provided in the vicinity of the latching strip 25.

Figure 11:
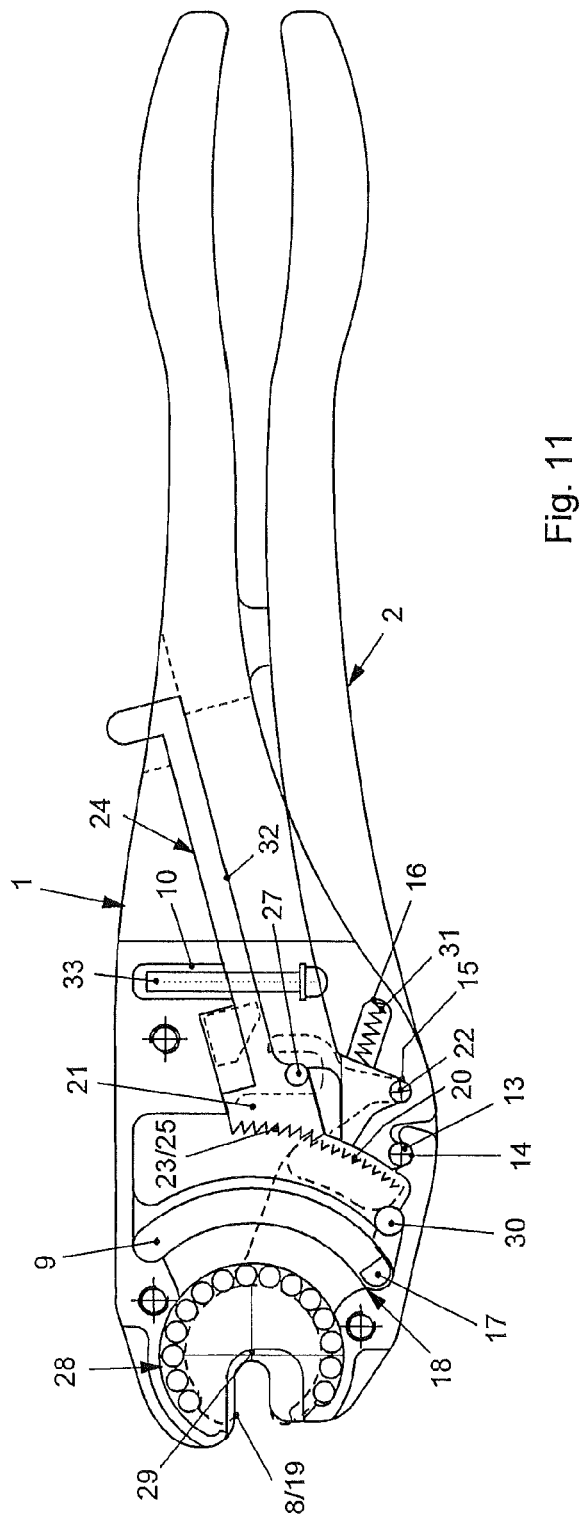
FIG. 11 shows a top view of the opened pliers according to FIG. 1 with the arrangement of the individual components.

The interaction between the individual components can be seen in particular in FIG. 11. The most important point in this case is that the cutting element 18 in the front region of the leg 1 of the pliers is inserted into a roller cage 28 and rotates in said roller cage 28. Said rotation is effected about a pivot point 19, a bottom of the jaw 8 of the pliers or of the cutting jaw 19 being arranged very close to said pivot point 29.

It can also be seen, moreover, that the cutting element 18 engages by way of its guide pin 17 into the guide channel 9 and is guided in said guide channel 9 in a radius about the pivot point 19. In addition, the cutting element 18 impacts against a stop 30 which is inserted into the receiving means 11.

The pressure element 2 sits with its pivot pin 13 in the pivot depression 14 and can be moved to a limited extent in relation to the leg 1 of the pliers. The pressure piece 21 is mounted in the depression 15 by means of the round piece 22 and is supported in the blind hole 16 by means of a helical spring 31. The toothed strip 23 of the pressure piece 21, in this case, interacts with the latching toothing 20 of the cutting element 18.

The fixing means 24 is inserted into a guide channel 32 in the leg 1 of the pliers and is mounted in said guide channel 32 so as to be displaceable. Its latching strip 25, in this case, covers at least in part the toothed strip 23 of the pressure piece 21. The stop cam 27 has the effect of not allowing the fixing means 24 to deflect rearward in an unwanted manner.

In addition, FIG. 11 indicates a bolt 33 which engages in the blind hole 10. Said bolt 33 can be spring-mounted such that the pressure element 2 is supported in a spring-mounted manner in relation to the leg 1 of the pliers.

The method of operation of the present invention is as follows:

For cutting a workpiece (not shown in any detail), said workpiece is inserted into the jaw of the pliers or the cutting jaw 8/19. The cutting element 18, in this case, is situated in the start position shown in FIG. 11 such that the jaw 8/19 is open as extensively as possible. The leg 1 of the pliers and the pressure element 2 are forced apart such that the toothed strip 23 of the pressure piece 21 engages the latching toothing 20 of the cutting element 18 by way of as large a number of teeth as possible. Said engagement is supported by pressure from the helical spring 31.

The pressure element 2 is then moved toward the leg 1 of the pliers, the pressure piece 21 entraining the cutting element 18 such that said cutting element, guided by the guide pin 17, rotates about the pivot point 19 in the guide channel 9 and in the roller cage 28. In this case, the inside clearance of the jaw of the pliers or of the cutting jaw 8/19 is reduced such that the cutting element 18 cuts into the workpiece. At the same time, the latching toothing 20 of the cutting element 18 runs down the latching strip 25 of the fixing means 24 and is held by said fixing means 24, when, for recovering, the pressure element 2 is then moved away from the leg 1 of the pliers again such that the toothed strip 23 of the pressure piece 21 is able to move along the latching toothing 20 and enters into a new region of said latching toothing 20.

The pressure element 2 can now be moved once again against the leg 1 of the pliers, the pressure piece 21 by means of the latching connection with the cutting element 18 entraining said cutting element and rotating about the pivot point 29. This occurs until the work piece has been cut through.

The invention claimed is:

1. A pair of pliers for cutting workpieces comprising at least one leg (1) and one pressure element (2) connected together by a pivot point (13), the leg (1) of the pliers is provided with a jaw (8) adapted to receive a workpiece, wherein the pair of pliers further includes a cutting element (18) with a cutting jaw (19), wherein a bottom of the jaw (8) of the leg and a bottom of the cutting jaw (19) are arranged in the vicinity of a further pivot point (29) about which the cutting element (18) rotates in the leg (1) of the pliers, the cutting element (18) has a latching toothing (20) located opposite the cutting jaw (19), the latching toothing (20) engages with a toothed strip (23) of a pressure piece (21), the pressure piece (21) or the toothed strip (23) is held engaged with the latching toothing (20) by means of a force storage means (31) which comprises a helical spring having two ends with one end pressing against the pressure piece and the other end held in a blind hole (16) in the pressure element (2).

2. A pair of pliers for cutting workpieces comprising at least one leg (1) and one pressure element (2) connected together by a pivot point (13), the leg (1) of the pliers is provided with a jaw (8) adapted to receive a workpiece, wherein the pair of pliers further includes a cutting element (18) with a cutting jaw (19), wherein a bottom of the jaw (8) of the leg and a bottom of the cutting jaw (19) are arranged in the vicinity of a further pivot point (29) about which the cutting element (18) rotates in the leg (1) of the pliers, the cutting element (18) has a latching toothing (20) located opposite the cutting jaw (19), the latching toothing (20) engages with a toothed strip (23) of a pressure piece (21), the pressure piece (21) or the toothed strip (23) is held engaged with the latching toothing (20) by means of a force storage means (31), wherein a round piece (22) is formed at a free end of the pressure piece (21) and is supported in a depression (15) formed in the pressure element (2).

3. The pliers as claimed in claim 1 or 2, wherein the latching toothing (20) has associated therewith a fixing means (24) with a further latching strip (25).

4. The pliers as claimed in claim 3, wherein the fixing means (24) is arranged to be displaceable in the leg (1) of the pliers.

5. The pliers as claimed in claim 1 or 2, wherein the cutting element (18) is arranged with a guide pin (17) in a guide channel (9) in the leg (1) of the pliers.

6. The pliers as claimed in claim 1 or 2, wherein the pressure element (2) comprises a leg and sits with the pivot pin (13) in a pivot channel (14) in the leg (1) of the pliers.

7. The pliers as claimed in claim 6, wherein the pressure element (2) is supported by a force storing means against the leg (1) of the pliers.

8. The pliers as claimed in claim 7, wherein the force storing means comprises a spring-mounted bolt (33).

\* \* \* \* \*